United States Patent
Ellis et al.

(10) Patent No.: US 11,730,848 B1
(45) Date of Patent: *Aug. 22, 2023

(54) GAS IRRADIATION APPARATUS AND METHOD

(71) Applicants: Stanley W. Ellis, Bakersfield, CA (US); Mitchell Caughron, Bakersfield, CA (US)

(72) Inventors: Stanley W. Ellis, Bakersfield, CA (US); Mitchell Caughron, Bakersfield, CA (US)

(73) Assignee: Environmental Technologies, LLC, Bakersfield, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/095,362

(22) Filed: Jan. 10, 2023

Related U.S. Application Data (63) Continuation-in-part of application No. 17/841,463, filed on Jun. 15, 2022, now Pat. No. 11,576,994.

(51) Int. Cl.
*A61L 9/20* (2006.01)
*A62B 9/00* (2006.01)
*A62B 7/10* (2006.01)

(52) U.S. Cl.
CPC ........ *A61L 9/20* (2013.01); *A62B 9/00* (2013.01); *A61L 2209/12* (2013.01); *A62B 7/10* (2013.01)

(58) Field of Classification Search
CPC .............. A61L 9/20; A62B 9/00; A62B 7/10
See application file for complete search history.

(56) References Cited

U.S. PATENT DOCUMENTS

| | | |
|---|---|---|
| 6,623,544 B1 | 9/2003 | Kaura |
| 6,983,745 B2 | 1/2006 | Tang et al. |
| 8,153,058 B2 | 4/2012 | Araiza et al. |
| 9,260,323 B2 | 2/2016 | Boodaghians et al. |
| 10,888,721 B2 | 1/2021 | Hur et al. |
| 11,033,644 B2 | 6/2021 | Wu et al. |
| 11,305,032 B2 | 4/2022 | Ellis et al. |
| 11,576,994 B1 | 2/2023 | Ellis et al. |
| 2006/0231100 A1 | 10/2006 | Walker et al. |
| 2007/0101867 A1 | 5/2007 | Hunter et al. |
| 2007/0102280 A1 | 5/2007 | Hunter et al. |

(Continued)

FOREIGN PATENT DOCUMENTS

| | | |
|---|---|---|
| JP | 2020044301 A | 3/2020 |
| WO | WO2020035666 A1 | 2/2020 |

*Primary Examiner* — Kevin Joyner
(74) *Attorney, Agent, or Firm* — James M. Duncan; Scanlon Duncan LLP (57) ABSTRACT

A gas irradiation system has an irradiation chamber having a plurality of compartments disposed circumferentially about a central axis. One of the compartments is an inlet compartment. The inlet compartment has an aperture at the bottom through which gas flows from the compartment. The irradiation chamber comprises a plurality of UV lights which are configured to irradiate the gas and neutralize pathogens as the gas flows through the irradiation chamber. Circumferentially adjacent to one side of the inlet compartment is an outlet compartment. Circumferentially adjacent in the opposite circumferential direction on the other side of the inlet compartment is the first of a plurality of intermediate compartments. These intermediate compartments extend circumferentially about the central axis between the inlet compartment and the outlet compartment.

20 Claims, 13 Drawing Sheets

(56) References Cited

U.S. PATENT DOCUMENTS

| | | |
|---|---|---|
| 2007/0181509 A1 | 8/2007 | Araiza et al. |
| 2010/0132715 A1 | 6/2010 | Litz |
| 2011/0114546 A1 | 5/2011 | Barsky et al. |
| 2012/0299456 A1 | 11/2012 | Horng |
| 2013/0128561 A1 | 5/2013 | Thomas et al. |
| 2013/0307549 A1 | 11/2013 | Liu |
| 2014/0264072 A1 | 9/2014 | Abbott et al. |
| 2016/0339133 A1 | 11/2016 | Lichtblau |
| 2017/0007385 A1 | 1/2017 | Wang |
| 2018/0028846 A1 | 2/2018 | Hur et al. |
| 2018/0104374 A1 | 4/2018 | Kim et al. |
| 2018/0250430 A1 | 9/2018 | Machovina et al. |
| 2020/0339441 A1 | 10/2020 | Wu et al. |
| 2021/0206664 A1 | 7/2021 | Bilenko et al. |
| 2021/0260559 A1 | 8/2021 | Yamazaki et al. |

GAS IRRADIATION APPARATUS AND METHOD

BACKGROUND OF THE INVENTION

The present invention generally relates to the treating gas to neutralize pathogens contained in the gas. More specifically, embodiments of the present invention relate to the neutralizing of pathogens contained in air inhaled by humans. Embodiments of the present invention may also be utilized for treating the exhalations of persons who may be infected with pathogens, including viruses, bacteria, fungi or other pathogens, where the exhalations may otherwise present a potential risk of harm to persons exposed to the exhalations. The recent and ongoing SARS-CoV-2 coronavirus epidemic has illustrated the need for effective devices and methods which can provide safe breathing air for first responders, caregivers, and essential personnel. Such devices may be configured into a package which is relatively small, lightweight, easy to use, and having self-contained power means. Alternatively, the devices may be configured as part of a heating, ventilation, and air conditioning ("HVAC") system for a building, vehicle, marine vessel or aircraft.

UVC light technology ("UV-C light") is a radiation method which makes use of specific wavelengths of ultraviolet light to neutralize pathogens. The wavelengths of UV-C light range from 200 to 300 nanometers. UV-C light is germicidal, which means it deactivates the DNA of microorganisms such as bacteria, viruses, and other pathogens, which disrupt the ability of the microorganisms to multiply and cause disease. UV-C light having a wavelength of 190-290 nm has also been found to be effective to inactivate spores of *Bacillus anthracis*. Given the robust nature of *Bacillus anthracis* and its relatively large single-cell size, an upstream filter should first be utilized. Once filtered, UV-C light can be effective in attacking the pathogen.

A variety of devices are known which utilize UV-C light for neutralizing pathogens. It is known that the level of neutralization of the pathogens is related to the exposure time of the pathogens to the UV-C light, and the distance of the UV-C light to the pathogens. An apparatus which provides effective exposure time and distance to multiple sources of UV-C light to a gas stream potentially carrying pathogens is desirable. It is also desirable that embodiments of such an apparatus are configurable as either a portable, lightweight, and self-contained system which may easily be carried and/or worn by first responders, caregivers, essential personnel, etc., or as components of an HVAC system for processing air circulated within enclosed spaces.

It would also be desirable to have a device which may also be configured to neutralize pathogens in the exhalations of an infected person, effectively quarantining the infected person from caregivers, family members and the like. Embodiments of the present invention provide an answer to these needs.

SUMMARY OF THE INVENTION

Embodiments of the presently disclosed gas irradiation system may purify incoming gas streams of pathogens and other biological material by utilizing UV LEDs as the gas stream flows through a plurality of radially adjacent compartments. The UV LEDs have germicidal wavelengths of 100-400 nm, and typically in the range of 100-280 nm. UV-C light having a wavelength of 190-290 nm has also been found to be effective to inactivate spores of *Bacillus anthracis*.

In some embodiments of the ultraviolet irradiation units the incoming gas stream is first filtered of air particulates, gases, vapors, and/or biological material by passing air through a high efficiency particulate air ("HEPA") filter to screen out particulates, gases, and vapors in addition to the pathogens. A HEPA filter should first be utilized in applications intended to inactivate *Bacillus anthracis*. Given the robust nature of *Bacillus anthracis* and its relatively large single-cell size, prefiltering an air stream containing this pathogen allows the UV-C light to inactivate remaining cells.

An embodiment of the presently disclosed air irradiation system has an irradiation chamber comprising a plurality of compartments disposed circumferentially about a central axis. Each compartment may have a top end and a bottom end. One of the compartments of the plurality of compartments is an inlet compartment and one of the compartments of the plurality of compartments is an outlet compartment which is radially adjacent to the inlet compartment. An inlet to the inlet compartment provides a conduit for a flow of a gas into the top end of the inlet compartment.

It is to be appreciated that because the apparatus is capable of reverse flow through the plurality of compartments, when the flow direction is reversed the "inlet" compartment will function as the "outlet" compartment and the "inlet" will function as an "outlet".

The bottom end of the inlet compartment has an aperture through which the flow of gas exits the inlet compartment (or the flow of gas enters the compartment in the case of reverse flow). Circumferentially adjacent on one side of the inlet compartment is an outlet compartment. Circumferentially adjacent in the opposite circumferential direction on the other side of the inlet compartment is the first of a plurality of intermediate compartments. These intermediate compartments extend circumferentially about the central axis between the inlet compartment and the outlet compartment. The compartments (inlet, outlet, and intermediate) have an open upper end and a bottom end. The bottom end of each compartment is sealed except for an aperture set within the bottom end to allow for gas to flow out of or into the compartment.

A plurality of UV LEDs having a germicidal wavelength of 100-400 nm, typically in the range of 100-280 nm, are disposed within the irradiation chamber and are configured to irradiate the flow of gas passing through the irradiation chamber. The UV LEDS may be adjacent to one or more of the apertures. In some embodiments, a UV LED may be disposed within or adjacent to each of the compartments. In other embodiments, the UV LEDs may be disposed in several, but not all of the compartments. For example, a UV LED may be disposed adjacent to each compartment, alternate compartments, every third compartment, or other configuration.

In some embodiments the UV LEDs may be connected to a controller which energizes selected UV LEDS according to the irradiation requirements of the particular gas flowing through the irradiation chamber. In some embodiments an optional UVC transparent glass lens, such as one fabricated from quartz, may be placed over each UV LED.

A top cover or comparable structure seals over the top ends of the compartments. The top cover has an underside having flow channels which provide for gas flow between the top ends of some pairs of adjacent compartments. Each flow channel may include an O-ring seal which encloses the flow channel to prevent intrusion of gas from other sources and to prevent release of gas from within the flow channel.

A bottom member seals over the bottom ends of the compartments, wherein the bottom member has an upper side which seals flow channels between the bottom ends of adjacent compartments. These flow channels may also utilize O-rings to prevent contamination or gas release.

Gas flow through the compartments may be driven by a pressure differential apparatus. In one embodiment of the apparatus, the pressure differential apparatus is a fan which is disposed upstream of the inlet compartment. Alternatively, the pressure differential apparatus may be a vacuum fan attached to the outlet compartment. A HEPA filter may be disposed upstream of the inlet compartment. For example, a positive pressure fan and filter may be placed immediately upstream of the inlet to the inlet compartment. Alternatively, a filter may be placed immediately upstream of the inlet to the inlet compartment and a vacuum fan connected to the outlet of the outlet compartment, with the vacuum fan applying a vacuum to all of the compartments.

In a normal flow operation, a flow of gas flows into and through the inlet compartment and exits the inlet compartment through the aperture at the bottom end. Upon exiting the inlet compartment, the flow of gas passes through a flow channel between the bottom of the inlet compartment and a first intermediate compartment, where the flow channels is sealed by the O-rings and structures of the bottom member. The flow of gas passes from the bottom to the top of the first intermediate compartment. The flow of gas passes through the top end of the first intermediate compartment through an upper flow path into the top of a circumferentially adjacent second intermediate compartment. Flow through the irradiation chamber proceeds sequentially through each of the circumferentially adjacent intermediate compartments, where irradiation may be applied to the flow gas stream at any point in the flow path, until the gas flows into the outlet compartment through the aperture at the bottom end of the outlet compartment and exits the irradiation chamber through the outlet at the upper end.

A reverse flow operation may be achieved by changing the direction of a fan or other pressure differential apparatus. In the reverse flow operation, the flow of gas enters the irradiation chamber through the outlet compartment, flows sequentially through the intermediate compartments in the same manner as discussed above, enters the inlet compartment at the aperture at the bottom end and exits the compartment through the "inlet" at the upper end.

The UV LEDs may be attached to the cover, in the walls of the compartments, or attached or disposed in the bottom member. The bottom member may also comprise a heat sink to dissipate the heat generated from the UV LEDS. The irradiation chamber may comprise a heat dissipation fan to further provide for cooling of the UV LEDs.

Each of the compartments may be in a cylindrical configuration and the irradiation chamber itself may be cylindrical. The compartments may be circumferentially disposed about a cylindrical storage compartment. A power source, such as a rechargeable battery, may be disposed within the cylindrical storage compartment. The UV LEDs, heat dissipation fan and the pressure differential apparatus may receive power from the power source.

The air irradiation system may further comprise a tube connected to the outlet compartment and a face mask attached to the tube. The air irradiation system may be packaged in an easily transportable carrying case for personal usage. Alternatively, embodiments of the irradiation chamber may be placed as a component of an HVAC system to purify an air stream being provided to an enclosure, such as a building, vehicle, marine vessel, or aircraft. In these applications, a plurality of irradiation chambers may be disposed either in a series or parallel configuration to provide for a high volume of flow through the system as required for the building, vehicle, marine vessel, or aircraft.

DETAILED DESCRIPTION OF THE INVENTION

Figure 1:
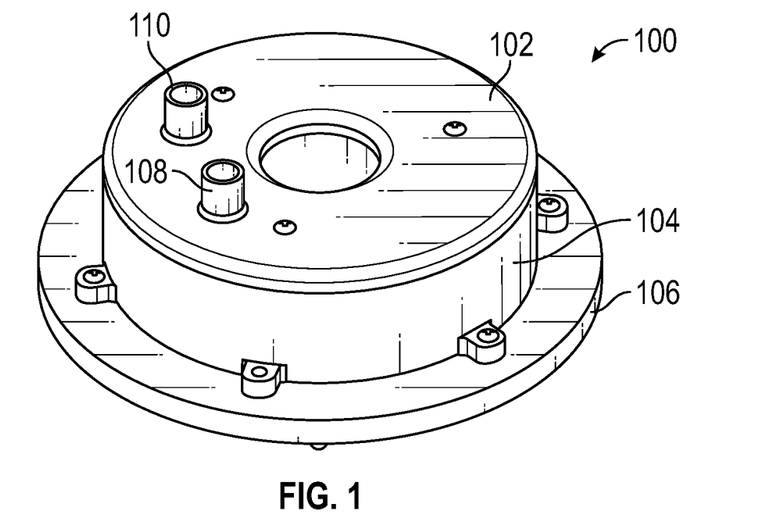
FIG. 1 depicts a perspective view of an embodiment of an irradiation chamber utilized with the currently disclosed gas irradiation system.
Figure 2:
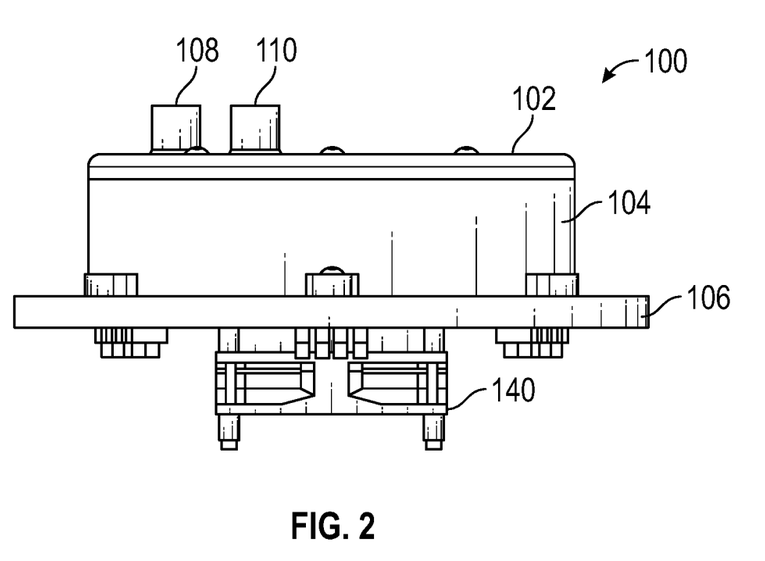
FIG. 2 depicts a front view of the irradiation chamber shown in FIG. 1.
Figure 3:
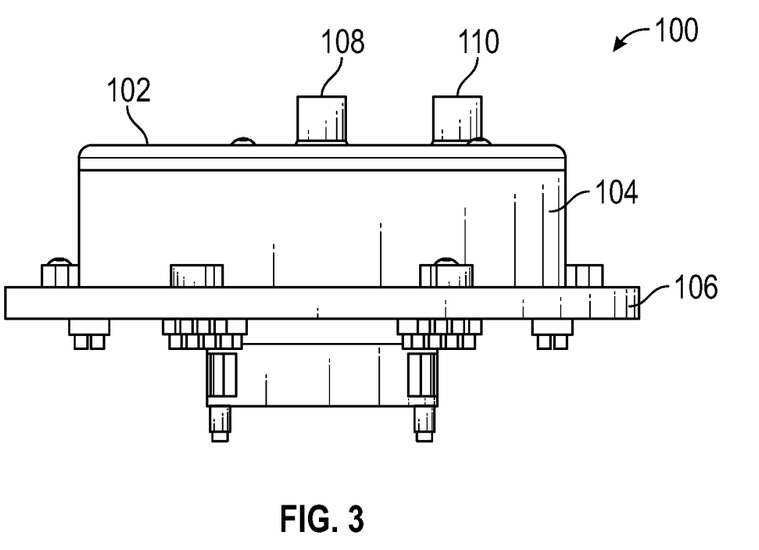
FIG. 3 depicts a side view of the irradiation chamber shown in FIG. 1.

Referring now to the Figures, FIG. 1 shows a perspective view of an embodiment of an irradiation chamber 100 which may be utilized with a gas irradiation system. While the gas irradiation system will typically be packaged as a self-contained unit for use by individuals, it is to be appreciated that components of the system may be utilized for irradiating gas streams for other applications. For example, irradiation chambers 100 may be configured in an HVAC system to irradiate a gas stream for a room, building, vehicle, aircraft, or marine vessel. In such application, multiple irradiation chambers may be configured in series or in parallel as required for the specific application. The term "gas" as used in the present disclosure will most typically be referring to atmospheric air. However, embodiments of the present invention may be utilized to neutralize pathogens in any gas stream.

As shown in FIGS. 1 through 4, irradiation chamber 100 may be packaged in a generally cylindrical configuration. However, it is to be appreciated that non-cylindrical configurations compatible with the sequential compartment arrangement discussed below may also be utilized. Embodiments of the Irradiation chamber 100 may comprise a cover 102, a housing 104, a bottom member 106, an inlet 108 and an outlet 110. Cover 102 may be secured to housing 104 with screws or other attachment means. Likewise, housing 104 may be secured to bottom member 106 with threaded fasteners.

Figure 4:
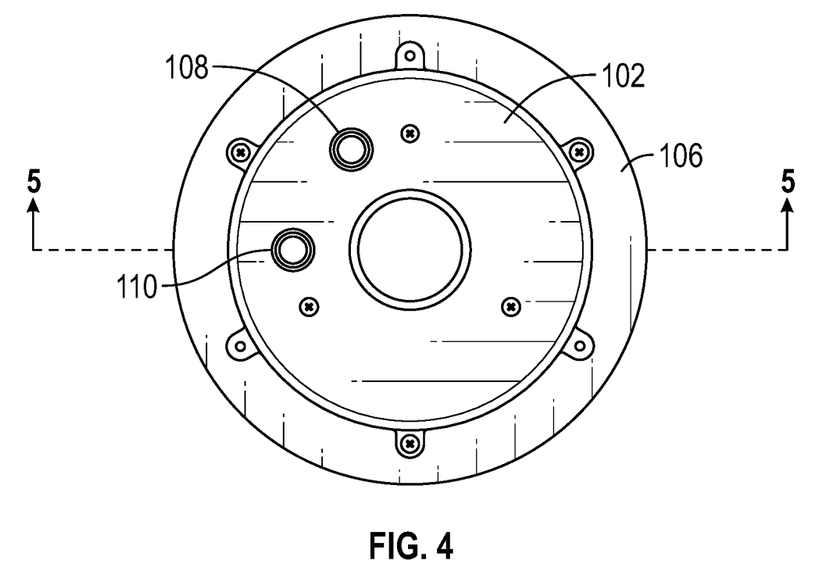
FIG. 4 depicts a top view of the irradiation chamber shown in FIG. 1.
Figure 5:
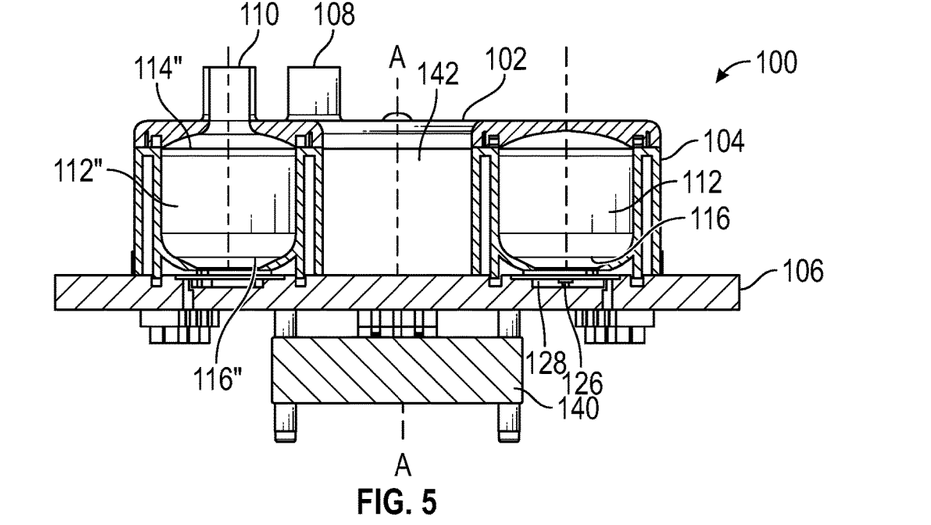
FIG. 5 shows a sectional view along line 5-5 of FIG. 4.
Figure 5A:
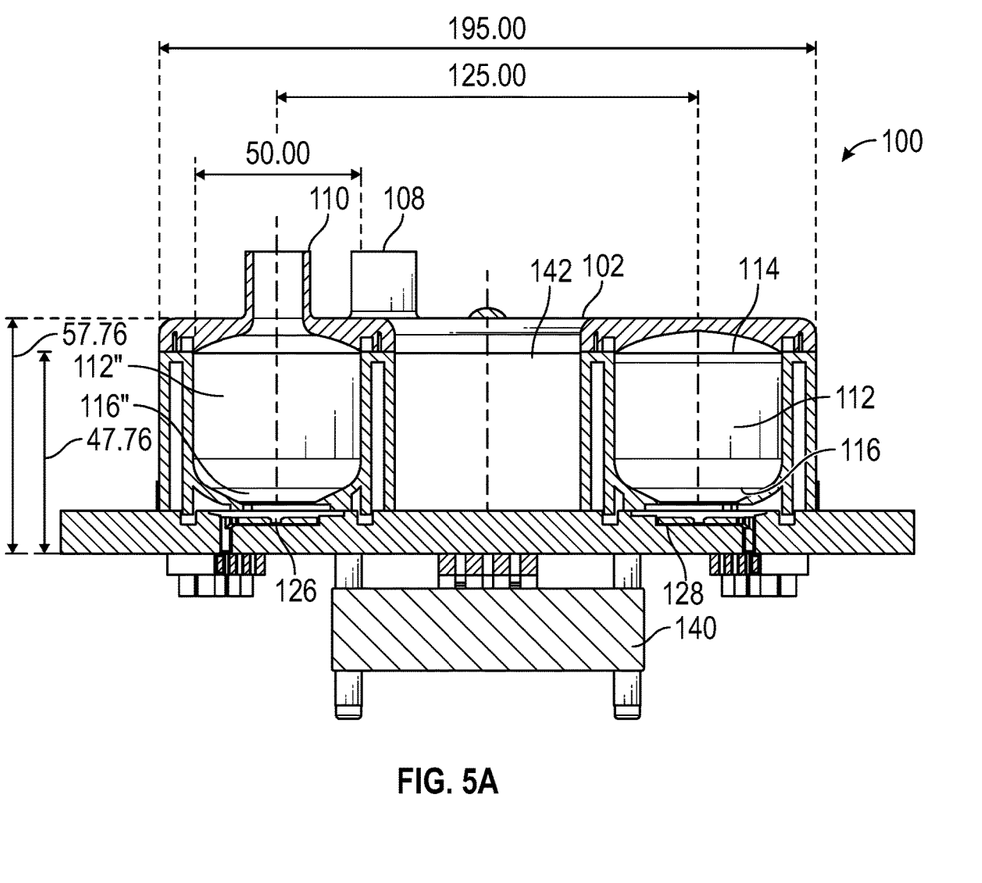
FIG. 5A shows a dimensioned sectional view for an embodiment of the irradiation chamber.

FIGS. 5 and 5A show sectional views along line 5-5 of FIG. 4, showing the abutting attachment of housing 104 to bottom member 106 which creates flow passages between adjacent compartments 112, which are positioned circumferentially about axis A.

Irradiation chamber 100 may further comprise a cylindrical storage compartment 142 about which compartments are positioned circumferentially. Among other possible uses, cylindrical storage compartment 142 may be utilized for storage of a power supply, such as a battery, for energizing a plurality of UV LEDS, a cooling fan, and/or a pressure differential apparatus utilized to provide gas flow through the irradiation chamber 100. FIGS. 5 and 5A show a cooling fan 140 attached to the underside of bottom member 106. The dimensions (in millimeters) shown in FIG. 5A depict an irradiation chamber which is sized to provide an airflow rate suitable for the breathing requirements of a single user, typically about 8 liters of air per minute. However, dimensions are provided for illustrative purpose only and are not intended in any way to limit the configuration of any embodiment of the invention for any application.

Figure 5B:
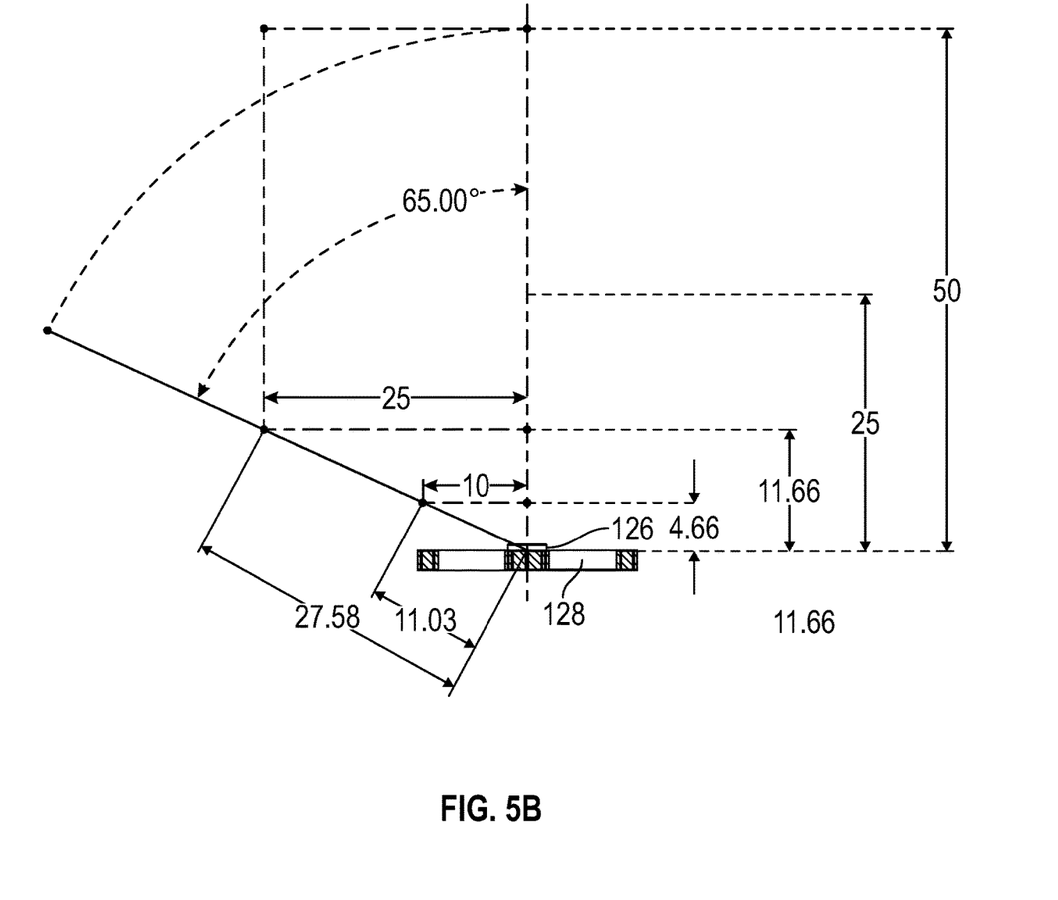
FIG. 5B depicts a dimensioned illumination profile within a compartment of an embodiment of an irradiation chamber.

For illustrative purposes, FIG. 5B depicts a dimensioned (in millimeters) illumination profile for a UV LED 126 which may be positioned at the bottom of a cylindrical compartment 112 within a chamber of an embodiment of an irradiation chamber. FIG. 5B illustrates how a gas flowing through an plurality of compartments may be exposed to UVC radiation in the illumination chamber.

Figure 6:
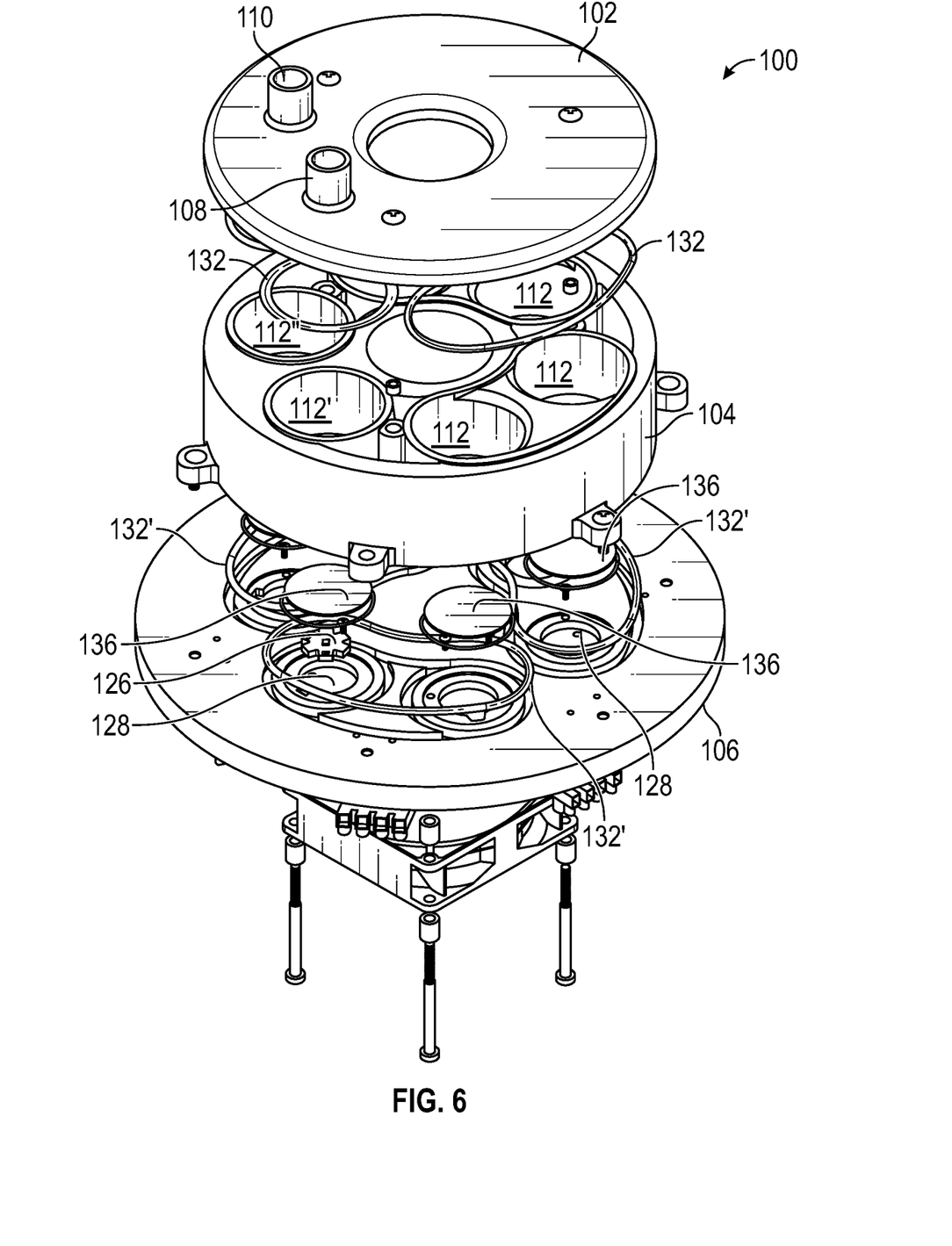
FIG. 6 depicts an exploded view of the irradiation chamber depicted in FIG. 1.

FIG. 6 depicts an exploded view of an irradiation chamber 100 of an embodiment of the present invention, showing an embodiment of an arrangement of the compartments 112 within housing 104 as per the present invention. The irradiation chamber 100 depicted in FIG. 6 comprises a plurality of compartments 112 which, as shown in FIG. 5, are disposed circumferentially about a central axis A which may comprise also be the central axis for cylindrical storage compartment 142. The plurality of compartments 112 includes an inlet compartment 112' which receives an inflowing gas stream through inlet 108, and an outlet compartment 112" which discharges an outflowing gas stream through outlet 110. As shown in the figures, inlet compartment 112' and outlet compartment 112" are circumferentially adjacent to one another. The remaining intermediate compartments 112 are circumferentially disposed in the opposite circumferential direction between inlet compartment 112' and outlet compartment 112".

Figures 13, 14:
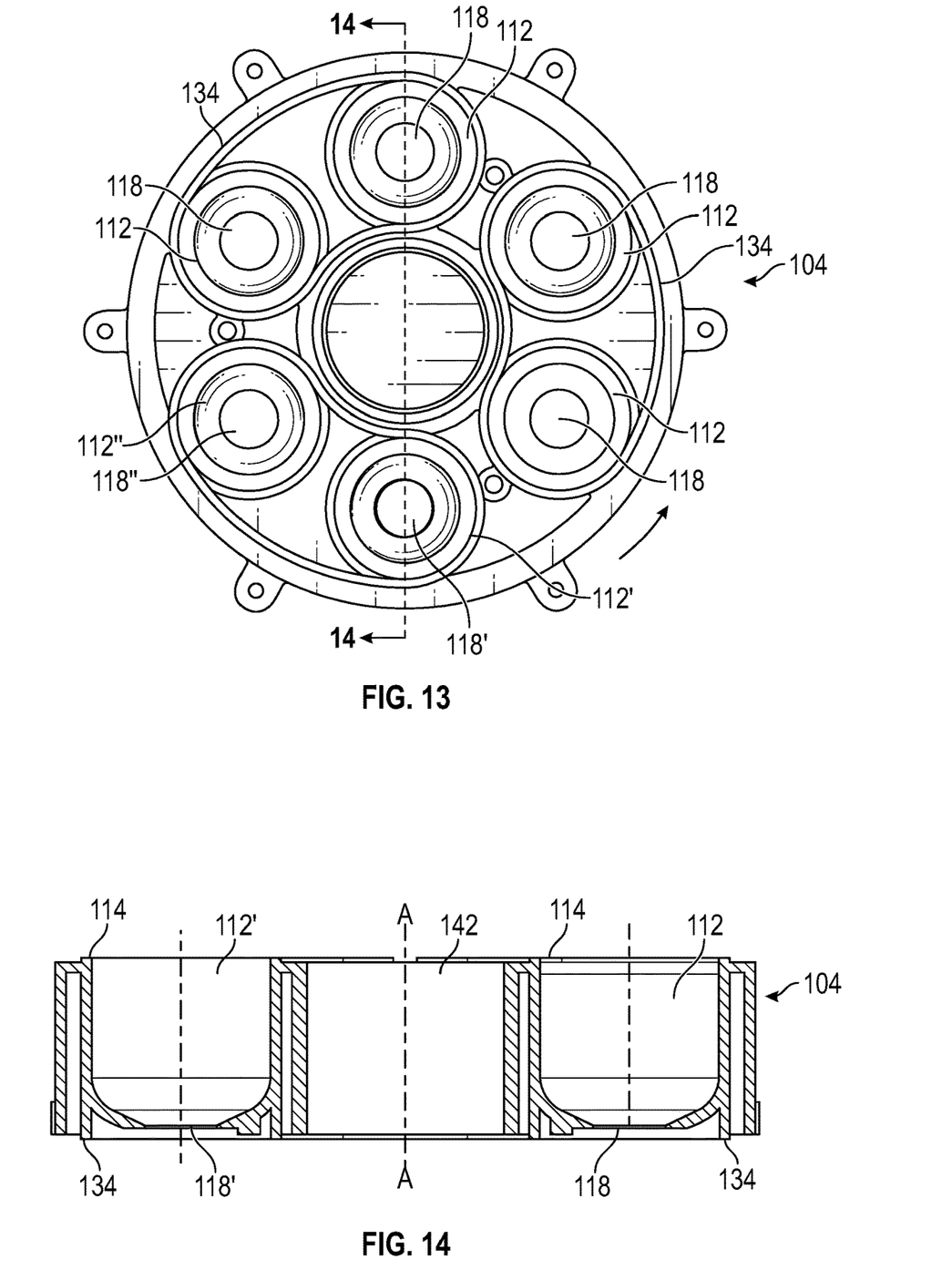
FIG. 13 shows a top view of the embodiment of the irradiation chamber body depicted in FIG. 12.
FIG. 14 is a sectional view of the irradiation chamber body taken along line 14-14 of FIG. 13.

A gas flowing through the irradiation chamber 100 flows sequentially through all of the compartments of irradiation chamber 100 starting at inlet compartment 112', through the plurality of intermediate compartments 112, into the outlet compartment 112" and flowing out of the irradiation chamber 100. The arrow on FIG. 13 shows the direction of flow beginning at compartment 112' as a gas stream flows counter-clockwise through the intermediate compartments 112 and arriving at outlet compartment 112". As the gas flows through the compartments, it is irradiated by a plurality of UV LEDs 126. As shown in FIG. 6, each compartment 112, 112', 112" may have a dedicated UV LED 126 positioned immediately adjacent to the bottom end 116 of each compartment. Alternatively, the UV LEDs 126 may be placed in other configurations, e.g. at every other compartment or set within the side walls of the compartments. Each UV LED 126 may be covered by a protective lens 136 which will typically be fabricated from quartz.

Flow through irradiation chamber 100 may be reversed by changing the direction of the pressure differential applied to the irradiation chamber, such that the gas flow enters the irradiation chamber 100 through outlet 110 into outlet compartment 112" through intermediate compartments 112 into inlet compartment 112' and exiting through inlet 108.

Figure 12:
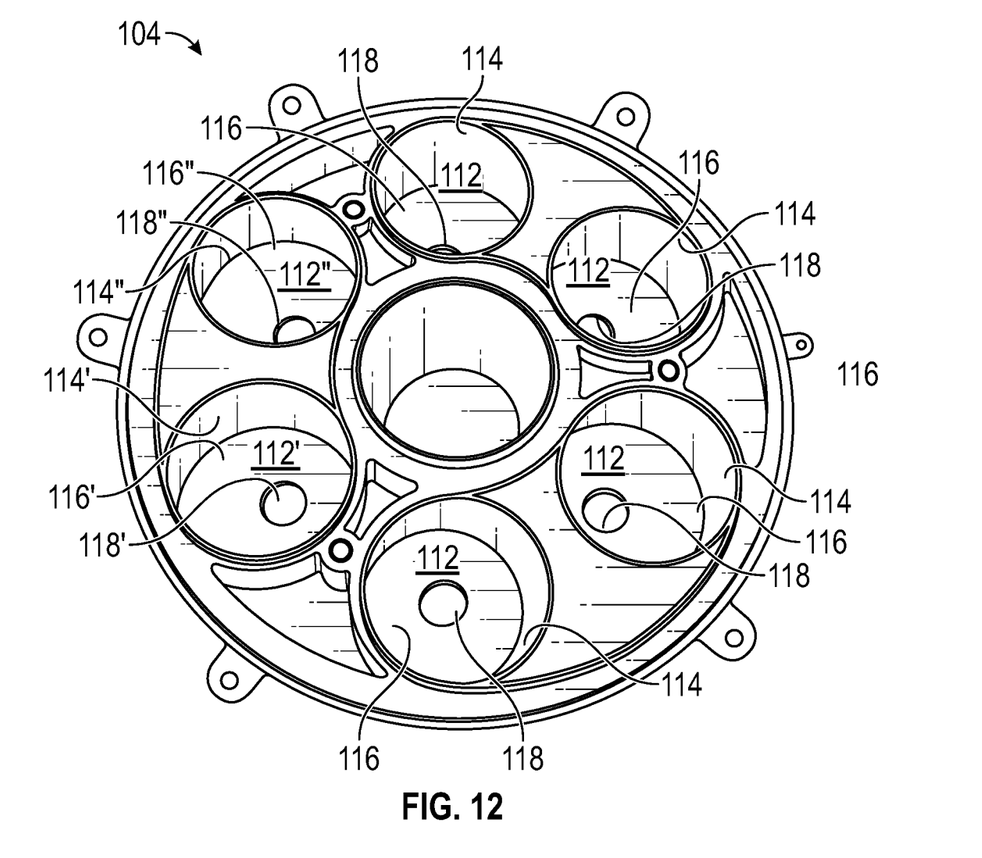
FIG. 12 depicts a top perspective view of an embodiment of the irradiation chamber body showing a configuration of the compartments disposed circumferentially about a central storage compartment.

As indicated in FIGS. 6 and 12, the compartments 112 may be in a cylindrical configuration. However, the compartments may be in a non-cylindrical configuration so long as the compartments are disposed circumferentially about a central axis and configured such that gas flows sequentially through all of the intermediate compartments 112 between the inlet compartment 112' and the outlet chamber 112"

Figure 15:
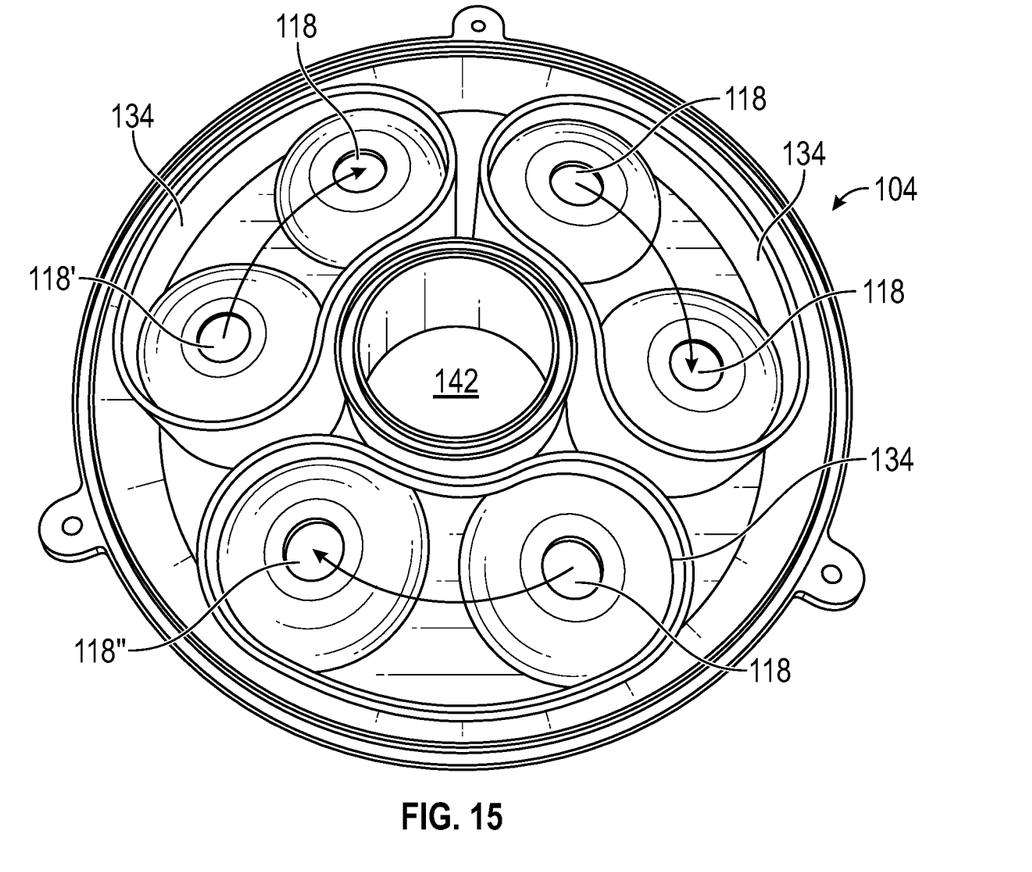
FIG. 15 depicts a bottom perspective view of the embodiment of the irradiation chamber body depicted in FIG. 12.

Each compartment 112 has an open top end 114 and a bottom end 116. Bottom end 116 is sealed except for an aperture 118 which penetrates through the bottom end 116 of each compartment 112 resulting in an opening in the underside of housing 104 as best shown in FIG. 15. As shown on FIG. 15, adjacent pairs of apertures 118 are enclosed on the underside of housing 104 by a seal wall 134 which may be generally configured in the shape of a kidney. A flow of gas which enters through inlet compartment 112' will flow out through aperture 118' and, because of the sealing of seal wall 134 by bottom member 106, will be directed to the circumferentially adjacent aperture 118 for entry into the circumferentially adjacent intermediate compartment 112. FIG. 15 indicates by the arrows the flow of gas between adjacent compartments until the gas flows into aperture 118" of outlet i compartment 112". It is to be appreciated that in a reverse flow situation, the flow of gas will be in the opposite direction indicated by the arrows shown in FIG. 15.

Figure 7:
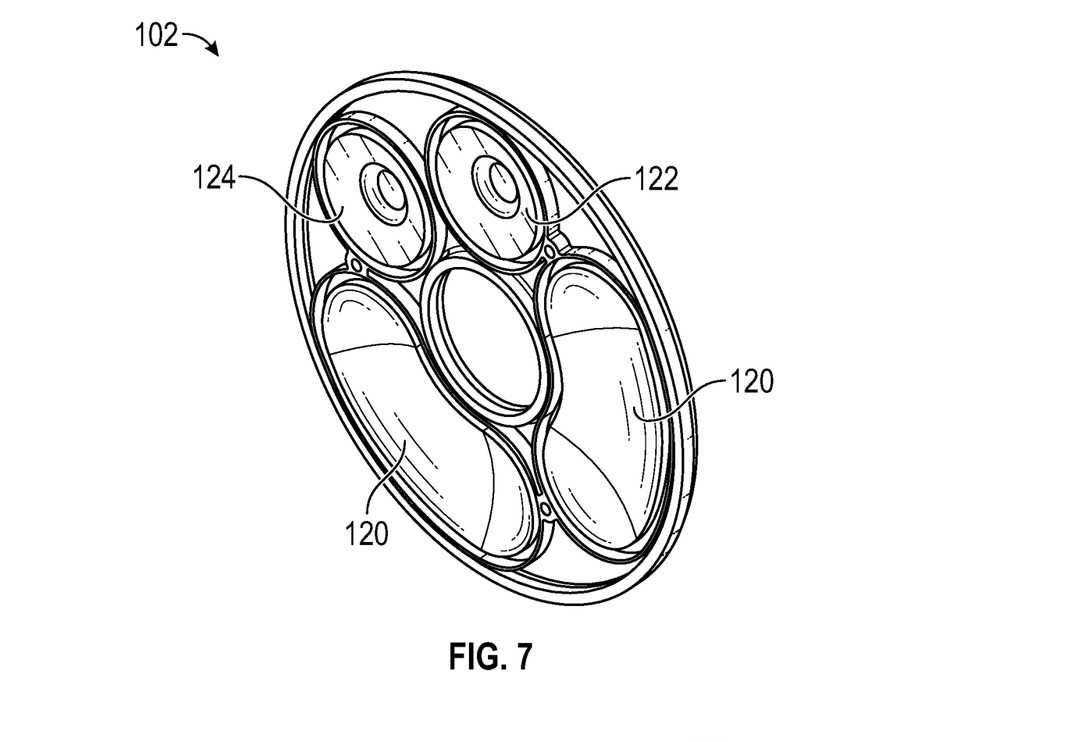
FIG. 7 depicts a perspective bottom view of an embodiment of a cover for the irradiation chamber depicted in FIG. 1.
Figure 8:
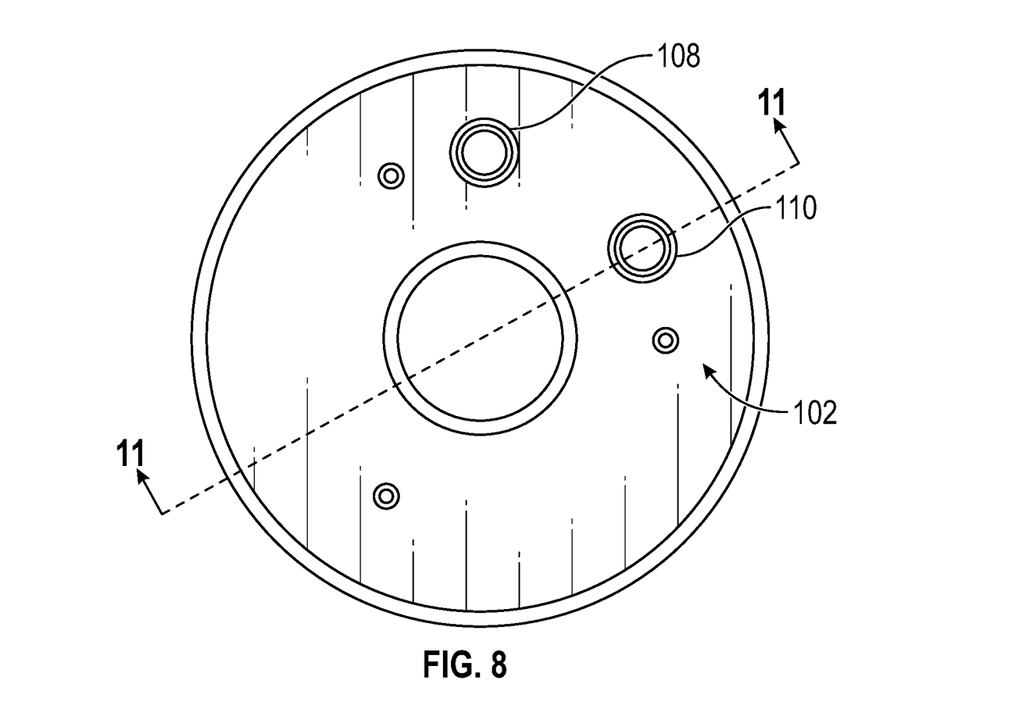
FIG. 8 depicts a top view of the cover for the irradiation chamber depicted in FIG. 7.
Figure 9:
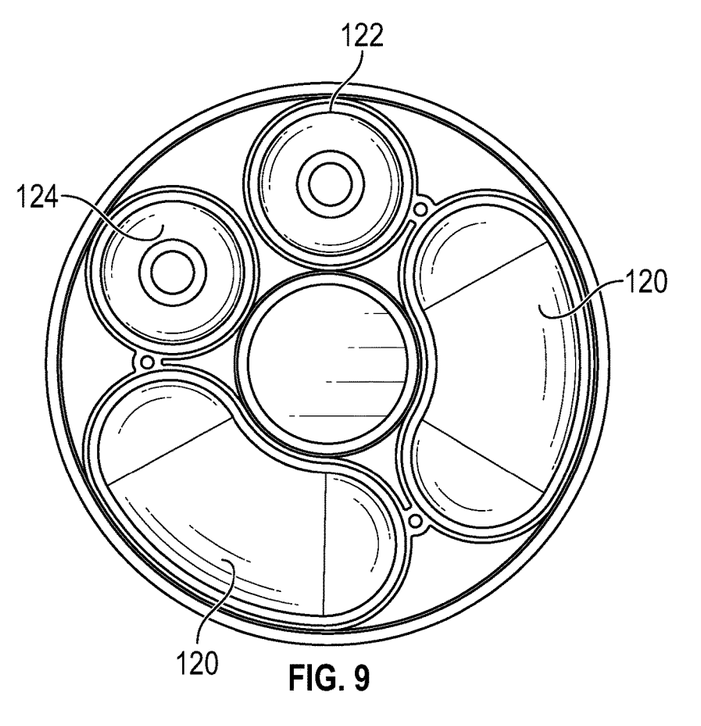
FIG. 9 depicts a bottom view of the cover for the irradiation chamber depicted in FIG. 7.
Figure 10:
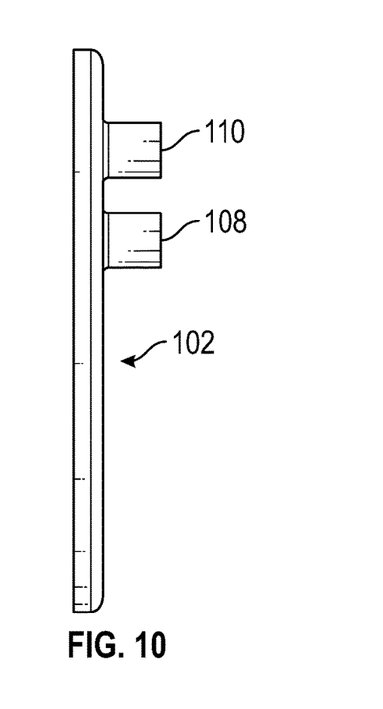
FIG. 10 shows a side view of the cover for the irradiation chamber depicted in FIG. 7.
Figure 11:
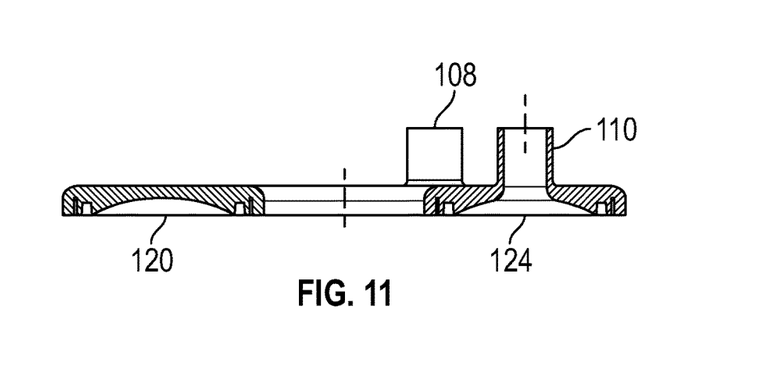
FIG. 11 depicts a sectional view taken along line 11-11 of FIG. 8.

FIGS. 12 through 15 depict an embodiment of a housing 104 for the irradiation chamber 100. The open ends 114 of the compartments 112 are sealed by cover 102, an embodiment of which is shown in FIGS. 7 through 11. Cover 102 has an underside having flow channels 120 which allow gas flow between the top ends 114 of adjacent pairs of intermediate compartments 112. Such flow channels 120 are depicted in FIGS. 7 and 9. As also shown in FIGS. 7 and 9, the underside of cover 102 has an inflow chamber 122 which covers the top end 114' of inlet compartment 112' and an outflow chamber 124 which covers the top end 114" of outlet compartment 112". O-rings 132 may be utilized to increase the sealing around flow channels 120, the inflow chamber 122, the outflow chamber 114 which are utilized to convey gas flow between the open top ends 114 of adjacent compartments.

Figure 16:
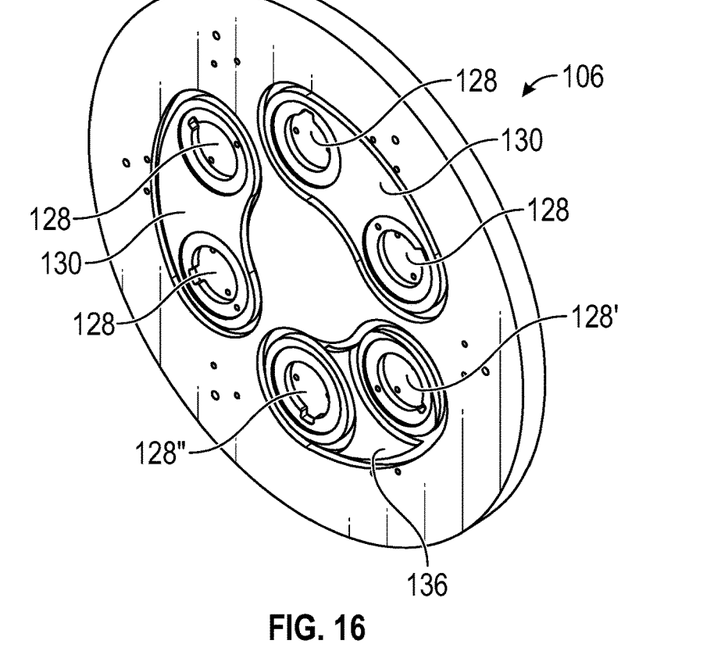
FIG. 16 is a top perspective view of a bottom member which seals against the bottom of the housing of the irradiation chamber.
Figure 17:
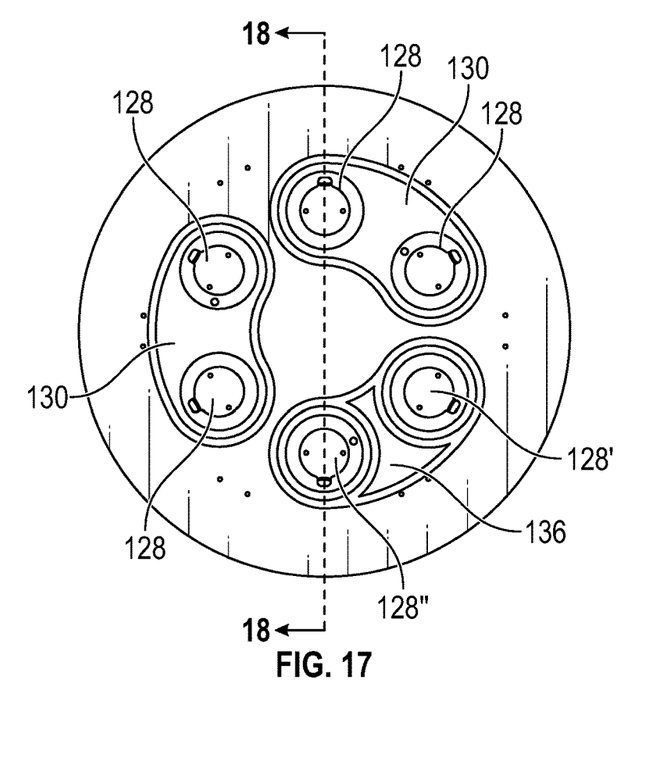
FIG. 17 is a top view of a bottom member which seals against the bottom of the housing of the irradiation chamber.
Figure 18:
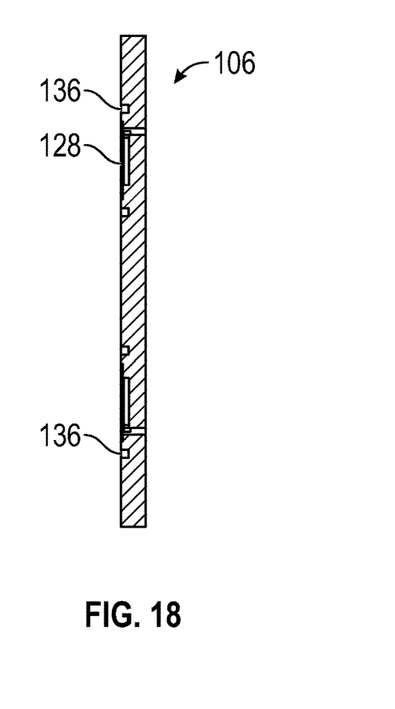
FIG. 18 is a sectional view of the bottom member taken along line 18-18 of FIG. 17.

The bottom ends 116 of compartments 112 are sealed off by bottom member 106 depicted in FIGS. 16 through 18.

which seals against the bottom of housing 104 and seal walls 134. An embodiment of bottom member 106 is shown in greater detail in FIGS. 16 through 18. Contoured O-ring groove 130 defines a generally kidney-shaped footprint around adjacent seats 128. O-rings 132' are disposed within contoured O-ring grooves 130 to prevent gas flow except between adjacent compartments 112 in the sequence described above. Bottom member 106 is attached to housing 104 such that aperture 118' of the inlet compartment 112' is positioned directly above seat 128' shown in FIGS. 16-17. When so positioned, aperture 118" of the outlet compartment 112" will be positioned directly above seat 128". Because it is desirable that none of the gas entering inlet compartment 112' leaks into outlet compartment 112", bottom member 106 may further comprise seal structure 136, which allows separate O-rings (not shown) to be placed around the seats 128', 128".

As suggested by the above description, when bottom member 106 is attached to the bottom of housing 104, seal walls 134 do not align with the generally kidney-shaped O-ring grooves around adjacent seats 128, but rather overlap.

Bottom member 106 may be utilized as a platform for UV LEDs 126 which may be seated in seats 128 of an upper side of bottom member 106. In order to redirect heat away from UV LEDs 126, bottom member 106 may be fabricated from a heat sink material such as copper or aluminum. Bottom member 106 may be fabricated with screw holes for retaining UV LEDs to the bottom member. Bottom member 106 may also have openings adjacent to seats 128 for running electrical leads and/or control wires to the UV LEDs 126.

Figure 19:
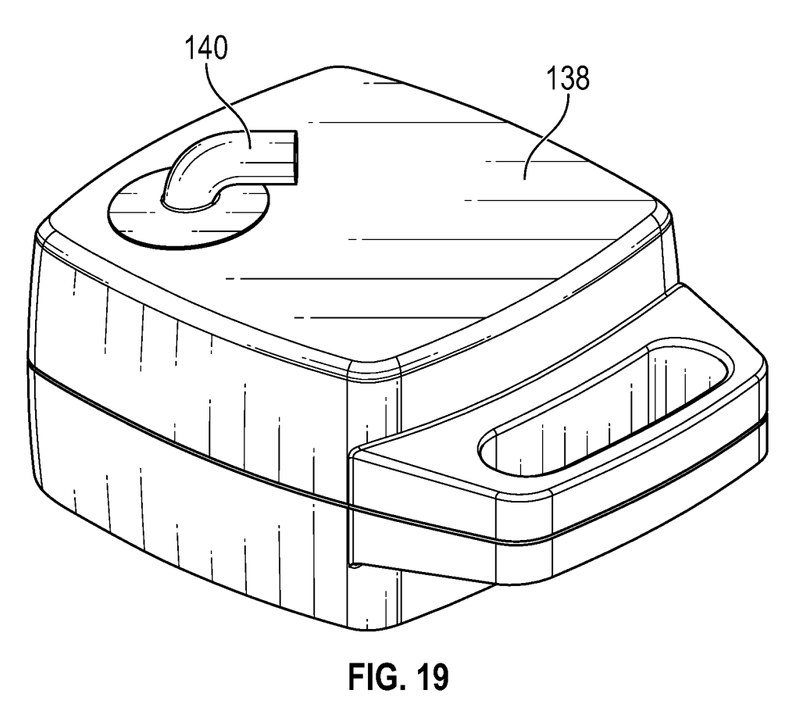
FIG. 19 depicts an embodiment of enclosure which may be utilized to house and transport the irradiation chamber.

FIG. 19 depicts a housing 138 which may be utilized to contain embodiments of irradiation chamber 100, showing an outlet 140 which receives irradiated gas from outlet 108 of the irradiation chamber. In addition to irradiation chamber 100, housing 138 may also contain a pressure differential apparatus, such as a positive pressure fan or vacuum fan for applying a pressure differential to irradiation chamber 100 to drive a gas flow through the irradiation chamber. Housing 138 may also contain a HEPA filter and filter carrier utilized to filter a gas entering the irradiation chamber. As indicated above, the flow direction through the irradiation chamber 100 may be reversed by changing the direction of the fan. In reverse flow operations, outlet 140 may be utilized to provide an inflow to the irradiation chamber.

Figure 20:
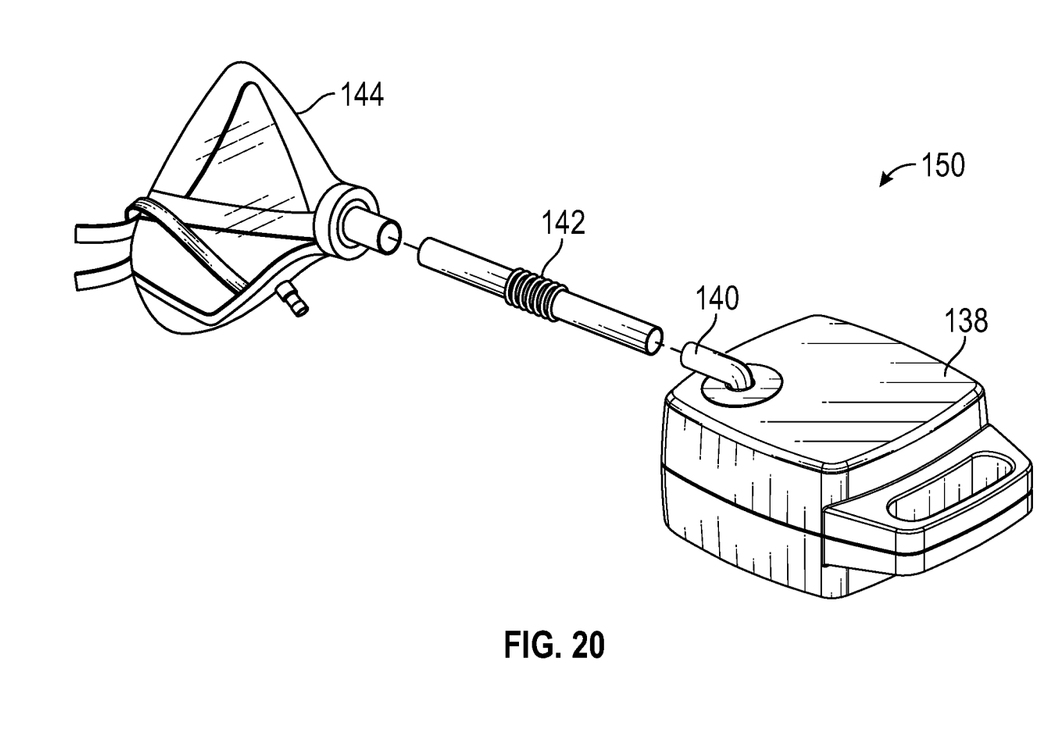
FIG. 20 depicts an embodiment of a personal breathing system of the presently disclosed invention.

FIG. 20 depicts an embodiment of a personal breathing system 150 of the presently disclosed invention which combines the irradiation chamber 100 contained within housing 138. A hose 142 is attached to outlet 140 of the housing 138 and a mask 144 attached to the hose. In reverse flow operation, exhalations containing pathogens may be directed into mask 144 and conveyed by hose 142 to the irradiation chamber 100 contained in the housing 138.

Having thus described the preferred embodiment of the invention, what is claimed as new and desired to be protected by Letters Patent includes the following:

1. A gas irradiation system comprising:
a housing member comprising a plurality of compartments disposed circumferentially about a central axis, the plurality of compartments comprising an inlet compartment, an outlet compartment, and a plurality of intermediate compartments disposed circumferentially between the inlet compartment and the outlet compartment, each compartment comprising an open top end and a bottom end, each bottom end comprising an aperture which penetrates the bottom end to form an opening for each compartment in an underside of the housing member;
a cover which seals the open top ends of the compartments, wherein the cover has an underside having a flow channel configured to provide an upper flow path between the top ends of an adjacent pair of compartments;
a bottom member having an upper side configured to provide a lower flow path between the bottom ends of an adjacent pair of compartments;
a plurality of light emitting diodes configured to irradiate a flow of gas as the flow of gas passes through the compartments;
wherein the upper flow path and the lower flow path are configured such that the flow of gas passes sequentially through the inlet compartment, through the plurality of intermediate compartments, into the outlet compartment.

2. The gas irradiation system of claim 1 wherein the underside comprises a seal wall which encloses the openings of adjacent compartments, the seal wall providing the lower flow path between the adjacent compartments.

3. The gas irradiation system of claim 2 wherein the light emitting diodes are mounted to the bottom member.

4. The gas irradiation system of claim 3 wherein the bottom member comprises a heat sink.

5. The gas irradiation system of claim 4 further comprising a heat dissipation fan attached to the bottom member.

6. The gas irradiation system of claim 1 wherein each of the compartments are cylindrical.

7. The gas irradiation system of claim 1 further comprising a tube connected to the oulet compartment.

8. The gas irradiation system of claim 7 further comprising a face mask attached to the tube.

9. The gas irradiation system of claim 1 wherein the housing is cylindrical.

10. The gas irradiation system of claim 1 wherein the plurality of compartments are disposed about a cylindrical housing.

11. The air irradiation system of claim 10 wherein the power source is disposed within the cylindrical housing.

12. A gas irradiation system comprising:
a housing comprising a central axis, the housing further comprising a plurality of compartments, the plurality of compartments individually disposed in a circumferential configuration about the central axis, the plurality of compartments comprising an inlet compartment and a circumferentially adjacent outlet compartment on a first side of the inlet compartment, and a plurality of intermediate compartments extending circumferentially between a second side of the inlet compartment and the outlet compartment; and
a plurality of ultraviolet light emitting diodes, wherein each of the ultraviolet light emitting diodes of the plurality of ultraviolet light emitting diodes is configured to progressively irradiate a flow of gas as it sequentially flows through the inlet compartment, the intermediate compartments, and the outlet compartment.

13. The gas irradiation system of claim 11 wherein each of the plurality of compartments is cylindrical.

14. The gas irradiation system of claim 12 further comprising a bottom member which attaches to a bottom end of each of the compartments of the plurality of compartments, wherein a flow channel is defined between the bottom ends of adjacent compartments and the bottom member, the flow channel configured to direct the flow of gas between adjacent compartments.

15. The gas irradiation system of claim 14 wherein the plurality of light emitting diodes are mounted to the bottom member.

16. The gas irradiation system of claim 12 wherein the plurality of compartments configured such that the flow of gas sequentially flows: (i) from a top of the inlet compartment to a bottom of the inlet compartment, (ii) into a bottom of a circumferentially adjacent first intermediate compartment to a top of the first intermediate compartment, (iii) into a top of a circumferentially adjacent second intermediate compartment to a bottom of the second intermediate circumferentially adjacent compartment, (iv) into a bottom of a third intermediate irradiation compartment to a top of the third intermediate irradiation compartment, (v) into the top of a circumferentially adjacent fourth intermediate irradiation compartment to the bottom of the fourth intermediate irradiation compartment, and (vi) into a bottom of the circumferentially adjacent outlet compartment to a top of the outlet compartment, the flow of gas exiting the outlet compartment through an outlet.

17. The gas irradiation system of claim 12 further comprising a tube connected to the outlet compartment.

18. The gas irradiation system of claim 17 further comprising a face mask attached to the tube.

19. A method of irradiating a stream of gas comprising the following steps:
directing the gas into an inlet of a housing, the housing comprising a plurality of compartments, the plurality of compartments individually disposed in a circumferential configuration about a central axis, the plurality of compartments comprising an inlet compartment and a circumferentially adjacent outlet compartment on a first side of the inlet compartment, and a plurality of intermediate compartments extending circumferentially between a second side of the inlet compartment and the outlet compartment; and
energizing a plurality of ultraviolet light emitting diodes, wherein the plurality of ultraviolet light emitting diodes is configured to progressively irradiate the flow of gas as the gas sequentially flows through the inlet compartment, the intermediate compartments, and the outlet compartment resulting in flow of an irradiated gas stream to an outlet of the outlet compartment.

20. The method of claim 19 wherein the plurality of compartments are configured such that the flow of gas sequentially flows: (i) from a top of the inlet compartment to a bottom of the inlet compartment, (ii) into a bottom of a circumferentially adjacent first intermediate compartment to a top of the first intermediate irradiation compartment, (iii) into a top of a circumferentially adjacent second intermediate compartment to the bottom of the second intermediate compartment, (iv) into a bottom of a circumferentially adjacent third intermediate compartment to a top of the third intermediate irradiation compartment, (v) into a top of a circumferentially adjacent fourth intermediate compartment to a bottom of the fourth intermediate compartment, and (vi) into a bottom of the circumferentially adjacent outlet compartment to a top of the outlet compartment, the flow of gas exiting the outlet compartment through an outlet.

* * * * *